United States Patent [19]

Ellis

[11] Patent Number: 4,463,149

[45] Date of Patent: Jul. 31, 1984

[54] SILICONE-CONTAINING CONTACT LENS MATERIAL AND CONTACT LENSES MADE THEREOF

[75] Inventor: Edward J. Ellis, Georgetown, Mass.

[73] Assignee: Polymer Technology Corporation, Wilmington, Mass.

[21] Appl. No.: 363,073

[22] Filed: Mar. 29, 1982

[51] Int. Cl.$^3$ .............................................. C08F 30/08
[52] U.S. Cl. .................................... 526/279; 523/106; 523/107
[58] Field of Search ................. 526/279; 523/106, 107

[56] References Cited

U.S. PATENT DOCUMENTS

| | | | |
|---|---|---|---|
| 4,152,508 | 5/1979 | Ellis et al. ............................ | 526/279 |
| 4,153,641 | 5/1979 | Deichert et al. ..................... | 526/264 |
| 4,189,546 | 2/1980 | Deichert et al. ..................... | 528/26 |
| 4,261,875 | 4/1981 | LeBoeuf ............................... | 523/107 |

Primary Examiner—Joseph L. Schofer
Assistant Examiner—J. M. Reddick
Attorney, Agent, or Firm—Wolf, Greenfield & Sacks

[57] ABSTRACT

According to the invention contact lenses are formed of polymerizable substituted alkyl and aryl siloxanes having one or more unsaturated, polymerizable groups. These compounds preferably contain substituted acetoxy or carbomethoxy groups which confer inherent wettability and high polarity. Novel organosiloxanes are provided particularly adaptable for use in forming contact lenses by themselves or copolymerized with other monomeric materials to form useful polymeric materials for contact lenses.

31 Claims, No Drawings

SILICONE-CONTAINING CONTACT LENS MATERIAL AND CONTACT LENSES MADE THEREOF

BACKGROUND OF THE INVENTION

Soft contact lenses can be divided into two basic types, water absorptive and non-water absorptive. Water absorptive lenses commonly are referred to as hydrogel lenses and are generally prepared from 2-hydroxyethyl methacrylate (HEMA) or copolymers with HEMA as the major component. High water content lenses have also been produced from vinylpyrrolidone. Non-water absorptive soft contact lenses are produced from silicone rubber or like materials. Such soft contact lenses can have one or more of the following disadvantages: poor durability, less visual acuity than hard lenses, poor oxygen permeability, and/or ease of bacterial contamination.

Hard contact lenses produced from polymethyl methacrylate (PMMA) have been known in the art for many years and offer the advantages of optical clarity, dimensional stability and durability. Although PMMA has been the standard of the hard contact lens industry, it has at least two drawbacks. Because PMMA is marginally hydrophilic a lens wearer may experience discomfort as a result of a foreign body reaction. Secondly, oxygen gas transport through PMMA contact lenses is extremely low which dictates that the lenses cannot be worn continuously for an extended period of time. Since the cornea receives its oxygen directly from the atmosphere the PMMA lens wearer often experiences corneal swelling and irritation due to prolonged oxygen deprivation.

Within the past ten years commercial cellulose acetate butyrate (CAB) has been utilized in an attempt to provide a hard contact lens that will transport oxygen. Although CAB exhibits modest oxygen permeability it lacks other essential qualities necessary for a contact lens material. The scratch or mar resistance of CAB contact lenses is poor which may be a reflection of the relative softness of CAB when compared to PMMA. Additionally, CAB lenses are often dimensionally unstable.

More recently, siloxane containing copolymers have been introduced as oxygen gas permeable hard contact lens materials. These polymeric compositions are generally prepared by copolymerizing methyl methacrylate with siloxanyl alkyl ester of methacrylic acid. Contact lenses containing substantial amounts of organosiloxane groups tend to be hydrophobic. Attempts to impart hydrophilic properties to such systems include the incorporation of a wetting agent and treatment of the lens surfaces. Incorporation of a wetting agent can improve the wettability of the lens but may also render the lens translucent when used in excessive amounts. Contact lenses containing such wetting agents can be tolerated by the wearer but tend to accumulate proteinaceous matter from the tear fluid. This results in decreased transparency of the lens and wearer discomfort. Surface treatment of the lens affords a wettable surface but can lack permanence. Any scratches or adjustments made on such lenses exposes the hydrophobic bulk material. Repeated surface treatment is then necessary which can be inconvenient.

The contact lens field has long known the advantages of silicone polymers for use in contact lenses. Poly(dimethylsiloxane) polymers are transparent and highly permeable to oxygen, although use of these polymers in contact lenses can present difficulties in the fabrication and finishing of lenses because of the rubbery nature of the polymers. Contact lenses produced from poly(dimethylsiloxane) are often inherently hydrophobic and often must be surface treated to render the surfaces wettable by tears.

It's known that the use of a methacrylate monomer containing a silicone moiety can be copolymerized with the standard monomer utilized in conventional hard contact lenses, i.e., methyl methacrylate, to obtain a copolymer of varying hardness values depending upon the ratio of hard and soft monomers employed. Thus, some attempts have been made in the art to produce hard oxygen-permeable contact lenses. For example, U.S. Pat. No. 3,808,178 discloses a copolymer of methyl methacrylate with a siloxanyl alkyl ester of methacrylic acid. The use of special wetting agents and cross-linking agents are also taught in U.S. Pat. No. 3,808,178.

In U.S. Pat. No. 4,152,508 the use of an itaconate ester copolymerized with a siloxanyl alkyl ester of methacrylic acid is disclosed. The siloxanyl alkyl ester provides for high permeability and the itaconate ester gives increased rigidity, hardness and some degree of wettability. In addition, specific cross-linking agents and hydrophilic monomers are incorporated which provide dimensional stability and wettability to contact lenses generated therefrom.

The compositions disclosed in U.S. Pat. Nos. 4,216,303 and 4,242,483 are branched siloxanyl alkyl esters of methacrylic acid essentially as suggested by the prior patents.

U.S. Pat. Nos. 4,153,641 and 4,189,546 teach the use of monomeric polysiloxanes end capped with activated, unsaturated groups. By varying the type and amount of comonomer as well as the moiety both hard and soft polymeric compositions are said to be possible. $\alpha,\omega$-bis-(4-methacryloxybutyl) polydimethylsiloxane is disclosed in which the poly(organosiloxane) moiety varies from about 0 to 800 units in length. For a hard contact lens the poly(organosiloxane) moiety should be of a rather short length, perhaps 0 to 10 units long, to avoid incompatibility in the final composition due to phase separation. Therefore, when comparing the monomeric polysiloxanes disclosed in both U.S. Pat. Nos. 4,153,641 and 4,189,546 with siloxanyl alkyl esters of methacrylic acid disclosed in U.S. Pat. Nos. 3,808,178 and 4,152,508, on the basis of utility in gas permeable hard contact lens compositions, similarities are noted. Whereas the siloxanyl alkyl esters of methacrylic acid disclosed in 3,808,178 and 4,152,508 are monomers, that is, contain one polymerizable unsaturated group, the monomeric polysiloxanes disclosed in 4,153,641 and 4,189,546 contain two such polymerizable unsaturated groups.

U.S. Pat. No. 4,259,467 discloses polysiloxanes containing hydrophilic side chains. These materials are generally rubbery and absorb water which makes them particularly suitable for soft contact lenses. The patent does teach the advantages of an inherently hydrophilic polysiloxane. U.S. Pat. No. 4,261,875 discloses polysiloxanes which contain hydroxyalkyl side chains which import hydrophilicity to the polymer. These polysiloxanes are copolymerized with other hydrophilic monomers to produce water absorbing compositions which are useful in soft contact lenses. Many of these prior art polysiloxanes are water absorbing to a degree greater than 2%. This can affect dimensional stability of contact lenses made with these materials.

SUMMARY OF THE INVENTION

It is an object of this invention to provide novel substituted alkyl or aryl siloxanes containing one or more unsaturated polymerizable groups which are particularly useful when polymerized alone or with modifying comonomers for optical contact lenses.

Still another object of this invention is to provide high quality optical contact lenses formed of substituted alkyl or aryl polysiloxanes containing one or more unsaturated or polymerizable groups and having high polarity with under about 2% water absorption and which tend to avoid the tendency to accumulate proteinaceous matter in use.

Still another object of this invention is to provide organosilanes in accordance with the preceding objects for use as contact lenses which are easily wettable.

According to the invention a substituted alkyl or aryl siloxane contains one or more unsaturated polymerizable groups and has the following formula:

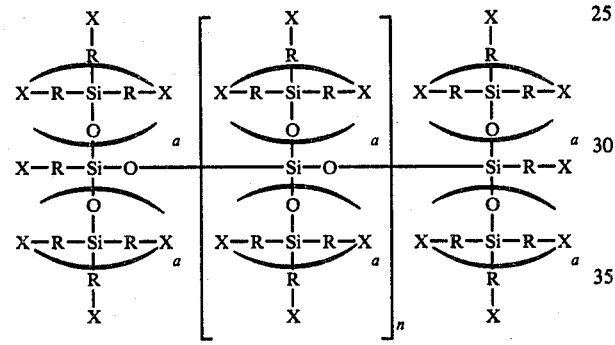

wherein:
X is an unsaturated polymerizable methacrylate or acrylate group or hydrogen or "Z" group;
R can be an alkylene or cycloalkylene group having from 1 to about 10 carbon atoms, or an arylene group. Each "R" group may be the same or different. The arylene group is preferably phenylene.
a is an integer from 0 to about 10 where each "a" may be the same or different.
n is an integer from 0 to about 10.
Z groups are acetoxy, carbomethoxy, glycidoxy, glyceryl, and carboxy. Acetoxy and carbomethyoxy groups are preferred. At least one "X" is a "Z" group.

The above siloxane can be polymerized by free radical polymerization as a homopolymer or with other monomers and materials to form contact lens materials useful for forming rods, buttons and machinable or otherwise formable into final contact lens products.

Particularly novel and useful siloxanes according to this invention are
1,3-bis(γ-methacryloxypropyl-1,1,3,3-tetra(3-acetoxypropyldimethylsiloxy)disiloxane
γ-methacryloxypropyl-tris(4-acetoxyphenyldimethylsiloxy)silane
γ-methacryloxypropyl-tris(2-carboxyethyldimethylsiloxy)silane
γ-methacryloxypropyl-tris(2-acetoxyethyldimethylsiloxy)silane
1-γ-methacryloxymethyl-3-(3-acetoxypropyl)-1,1,3,3-tetramethyldisiloxane
γ-methacryloxypropyl-bis(trimethylsiloxy)-(3-acetoxypropyldimethylsiloxy)silane
γ-methacryloxypropyl-bis(trimethylsiloxy)-(3-carbomethoxypropyldimethylsiloxy)silane
γ-methacryloxypropyl-bis(trimethylsiloxy)-(3-hydroxypropyldimethylsiloxy)silane
γ-methacryloxypropyl-bis(trimethylsiloxy)-(3-carboxypropyldimethylsiloxy)silane
γ-methacryloxypropyl-bis(3-acetoxypropyldimethylsiloxy)-(trimethylsiloxy)silane
γ-methacryloxypropyl-bis(3-carbomethoxypropyldimethylsiloxy)-(trimethylsiloxy)silane
γ-methacryloxypropyl-bis(3-hydroxypropyldimethylsiloxy)-(trimethylsiloxy)silane
γ-methacryloxypropyl-bis(3-carboxypropyldimethylsiloxy)-(trimethylsiloxy)silane
γ-methacryloxypropyl-tris(3-acetoxypropyldimethylsiloxy)silane
γ-methacryloxypropyl-tris(3-carbomethoxypropyldimethylsiloxy)silane
γ-methacryloxypropyl-tris(3-hydroxypropyldimethylsiloxy)silane
γ-methacryloxypropyl-bis(pentamethyldisiloxanyl)-(3-acetoxypropyldimethylsiloxy)silane
γ-methacryloxypropyl-bis(pentamethyldisiloxanyl)-(3-carbomethoxypropyldimethylsiloxy)silane
γ-methacryloxypropyl-bis(pentamethyldisiloxanyl)-(3-hydroxypropyldimethylsiloxy)silane
γ-methacryloxypropyl-bis(pentamethyldisiloxanyl)-(3-carboxypropyldimethylsiloxy)silane
1-(γ-methacryloxypropyl)-3-(3-acetoxypropyl)-tetra(trimethylsiloxy)disiloxane
1-(γ-methacryloxypropyl)-3-(3-carbomethoxypropyl)-tetra(trimethylsiloxy)disiloxane
1-(γ-methacryloxypropyl)-3-(3-hydroxypropyl)-tetra(trimethylsiloxy)disoloxane
1-(β-methacryloxypropyl)-3-(3-carboxypropyl)-tetra(trimethylsiloxy)disiloxane It is a feature of this invention that contact lenses formed from the siloxanes of this invention have a substantial content of organosiloxane to provide sufficient oxygen transport to the cornea. Good oxygen permeability in accordance with the materials of this invention includes oxygen permeability in the range of from 25 to 300 cm$^3$ mm/cm$^2$sec cm Hg$\times 10^{-10}$ for all contact lens materials.

In addition to high oxygen permeability, contact lenses and materials of this invention can be easily fabricated and finished, are dimensionally stable, inherently wettable, have high light transmission, are durable, biocompatible, non-hydrating, chemically stable and highly resistant to proteinaceous accumulation as well as being scratch resistant. The contact lenses can be worn safely and comfortably for extended periods of time while providing the wearer with good vision.

DESCRIPTION OF PREFERRED EMBODIMENTS

The contact lenses formed from organosiloxanes in accordance with this invention can be of the known types. Thus hard or soft contact lenses can be formed using conventional machining, casting or molding techniques to form contact lenses from blanks, rods and batches of materials made in accordance with conventional practice.

The organosiloxanes of this invention can be homopolymerized or copolymerized with each other. Other materials can be added to the contact lens materials as copolymers and include hardening agents, hydrophilic wetting agents and other additives such as tinting agents and the like.

It is preferred that the polyorganosiloxanes formed into contact lens materials and subsequent contact lenses in accordance with this invention be inherently hydrophilic in nature. This provides uniformly hydrophilic surfaces on contact lenses formed. Such contact lenses then exhibit less tendency to accumulate proteinaceous matter and provide the wearer with long-lasting comfort and visual acuity. The water absorption of such lenses is preferably at or under 2% making it substantially non-water absorbent although hydrophilic thereby aiding and allowing great dimensional stability.

The materials are inherently more polar in nature than those presently utilized in contact lenses. The added polarity aids in the hydrophilic nature of the lenses and also reduces the tendency for accumulation of mucoproteins.

The preferred alkyl or aryl siloxanes containing one or more unsaturated polymerizable groups in accordance with the present invention have the following formula:

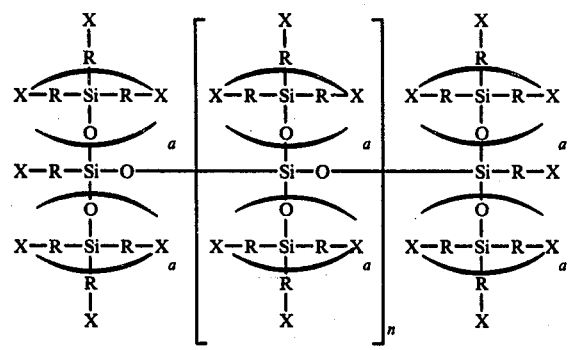

wherein:
X is an unsaturated polymerizable methacrylate or acrylate group or hydrogen or "Z" group;
R can be an alkylene or cycloalkylene group having from 1 to about 10 carbon atoms, or an arylene group, Each "R" group may be the same or different. The arylene group is preferably phenylene.
a is an integer from 0 to about 10 where each "a" may be the same or different.
n is an integer from 0 to about 10.
Z groups are acetoxy, carbomethoxy, glycidoxy, glyceryl, and carboxy. Acetoxy and carbomethyoxy groups are preferred. At least one "X" is a "Z" group.

Preferably X is a Z group which is in turn an acetoxy or carbomethoxy group. The higher the acetoxy or carbomethoxy content, the higher the tendency to obtain softer more wettable materials.

Particularly useful materials for forming into contact lenses in accordance with this invention are the following:

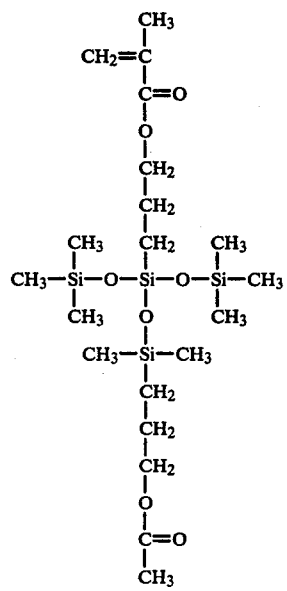

γ-methacryloxypropyl-bis(trimethylsiloxy)-(3-acetoxypropyldimethylsiloxy)silane

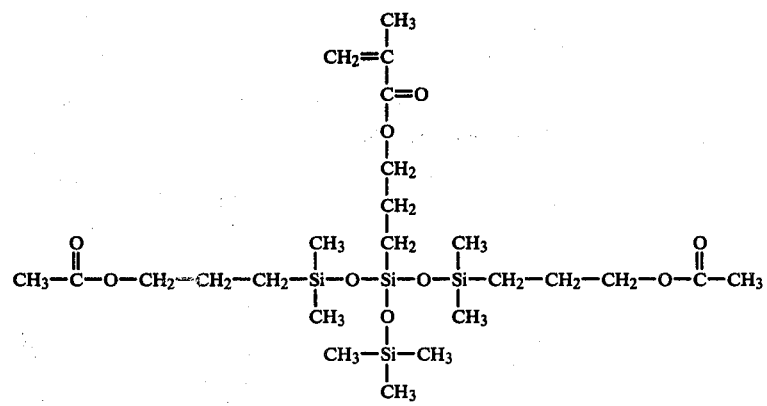

γ-methacryloxypropyl-bis(3-acetoxypropyldimethylsiloxy)-(trimethylsiloxy)silane

-continued
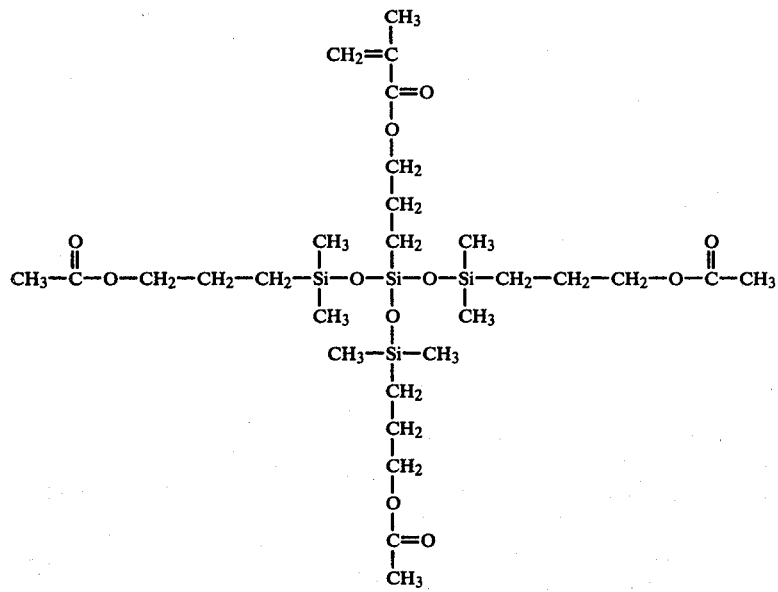
γ-methacryloxypropyl-tris(3-acetoxypropyldimethylsiloxy)silane
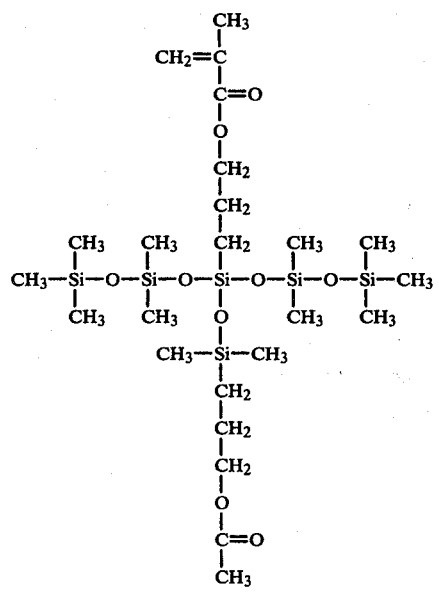
γ-methacryloxypropyl-bis(pentamethyldisiloxanyl)-
(3-acetoxypropyldimethylsiloxy)silane

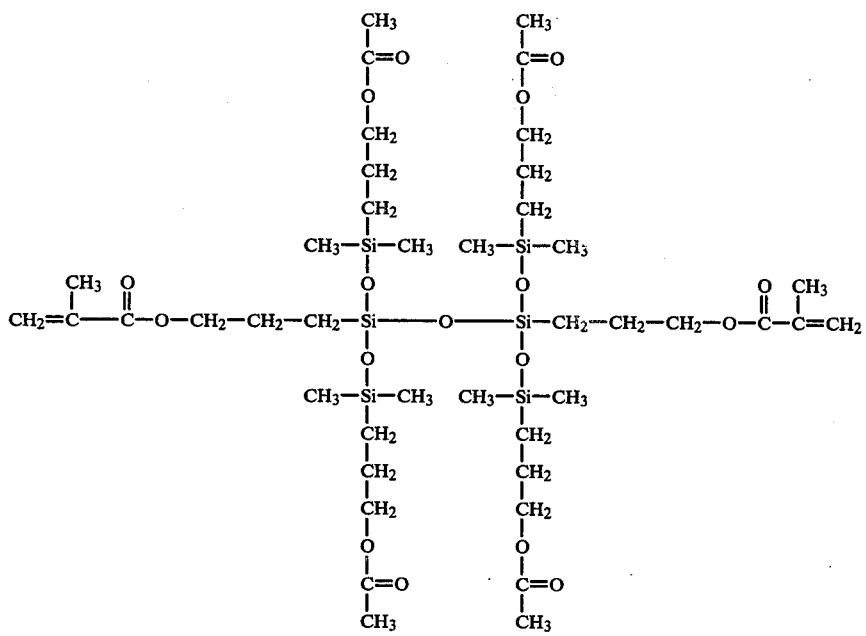
1,3-bis(γ-methacryloxypropyl)-1,1,3,3 tetra(3-acetoxypropyldimethylsiloxy)disiloxane
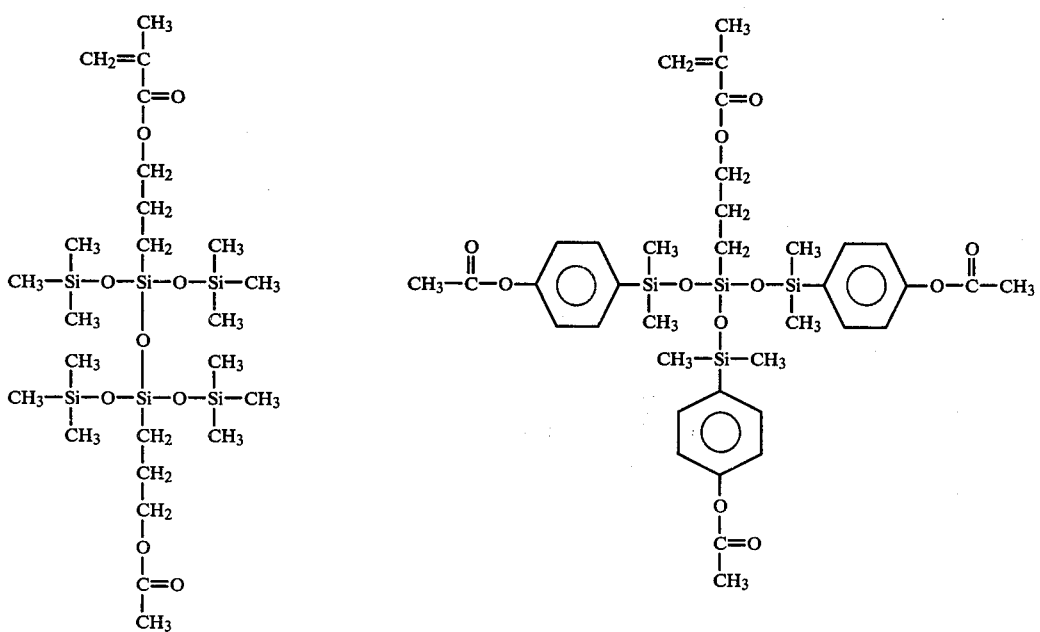
1-(γ-methacryloxypropyl)-3-(3-acetoxypropyl)-tetra(trimethylsiloxy)disiloxane
γ-methacryloxypropyl-tris(4-acetoxyphenyldimethylsiloxy)silane -continued

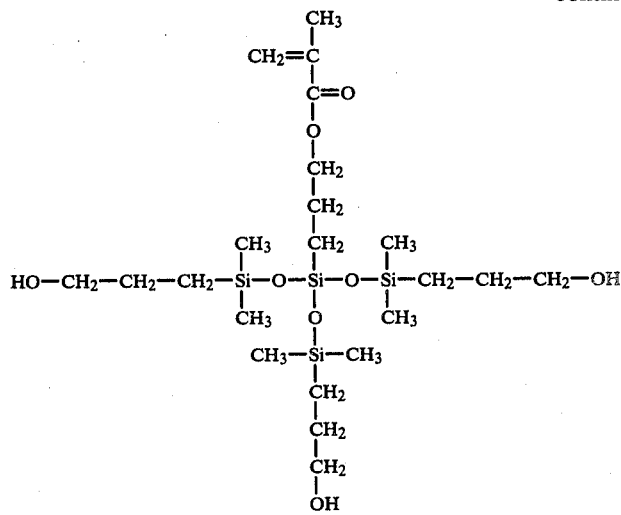

γ-methacryloxypropyl-tris(3-hydroxypropyldimethylsiloxy)silane

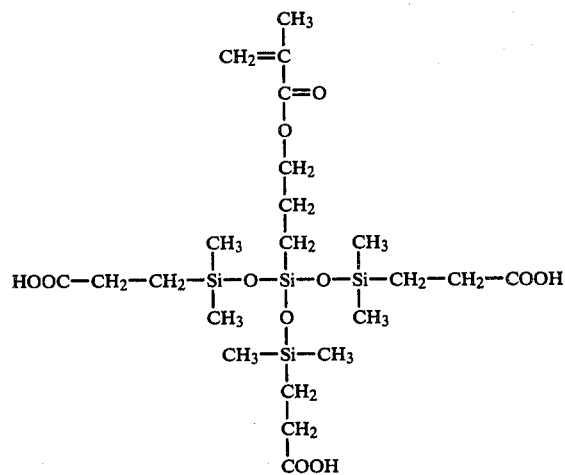

γ-methacryloxypropyl-tris(2-carboxyethyldimethylsiloxy)silane

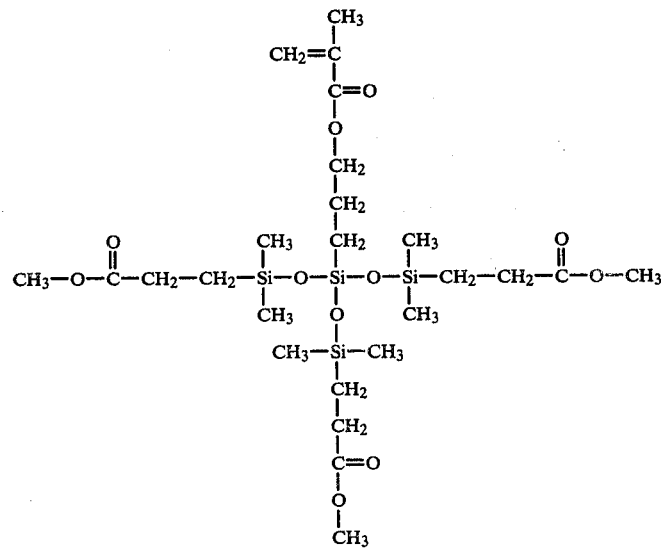

γ-methacryloxypropyl-tris(2-acetoxyethyldimethylsiloxy)silane

γ-methacryloxypropyl-bis(trimethylsiloxy)-(3-carbomethoxypropyldimethylsiloxy)silane

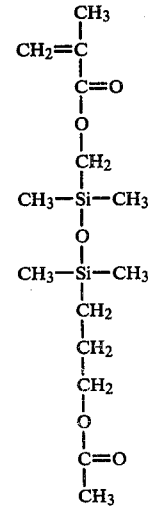

1-γ-methacryloxymethyl-3-(3-acetoxypropyl)-1,1,3,3-tetramethyldisiloxane

γ-methacryloxypropyl-bis(trimethylsiloxy)-(3-hydroxypropyldimethylsiloxy)silane

γ-methacryloxypropyl-bis(trimethylsiloxy)-(3-carboxypropyldimethylsiloxy)silane
γ-methacryloxypropyl-bis(3-carbomethoxypropyldimethylsiloxy)-(trimethylsiloxy)silane
γ-methacryloxypropyl-bis(3-hydroxypropyldimethylsiloxy)-(trimethylsiloxy)silane
γ-methacryloxypropyl-bis(3-carboxypropyldimethylsiloxy)-(trimethylsiloxy)silane
γ-methacryloxypropyl-tris(3-carbomethoxypropyldimethylsiloxy)silane
γ-methacryloxypropyl-bis(pentamethyldisiloxanyl)-(3-carbomethoxypropyldimethylsiloxy)silane
γ-methacryloxypropyl-bis(pentamethyldisiloxanyl)-(3-hydroxypropyldimethylsiloxy)silane
γ-methacryloxypropyl-bis(pentamethyldisiloxanyl)-(3-carboxypropyldimethylsiloxy)silane
1-(γ-methacryloxypropyl)-3-(3-carbomethoxypropyl)-tetra(trimethylsiloxy)disiloxane
1-(γ-methacryloxypropyl)-3-(3-hydroxypropyl)-tetra(trimethylsiloxy)disiloxane
1-(γ-methacryloxypropyl)-3-(3-carboxypropyl)-tetra(trimethylsiloxy)disiloxane It is understood that the examples given above should not limit the invention to substituted alkyl siloxanes since substituted phenyl groups, cyclohexyl and other groups are useful in this invention either alone or in combinations. Also, it is understood that each "X" group shown in the general structure may be the same or different.

Preferably "X", the unsaturated polymerizable groups, is chosen from among:
methacryloxy
acryloxy Preferably "R", when a divalent alkyl group, is chosen from among:
methylene
ethylene
propylene
butylene
cyclohexylene When "R" is aryl in nature the entire "R-X" unit can be chosen from among:
substituted phenyl groups
substituted benzyl groups
substituted phenethyl groups
substituted tolyl groups
substituted xylyl groups The novel siloxane monomers employed in this invention are prepared utilizing techniques widely known in the art.

The comonomers used to modify the preferred siloxane materials of this invention when used, are those which are capable of undergoing free radical polymerization and enhance a desirable property such as machinability, durability, biocompatibility and hardness.

The term "hardening agent" as used in this application is meant to include comonomers which vary the hardness of copolymers formed with the siloxanes of this invention. Thus certain hardening agents can in fact cause a copolymeric material of this invention to be harder or softer than the siloxane if homopolymerized.

The derivatives of acrylic, methacrylic and itaconic acid such as esters of a $C_1$-$C_{20}$ monohydric or polyhydric alkanol or phenol and an acid selected from the class consisting essentially of acrylic and methacrylic acid, itaconate mono or diester or other known derivatives can be used as comonomers to act as hardening agents. Such hardening agents include:

methyl acrylate
methyl methacrylate
mono or di methyl itaconate
ethyl acrylate
ethyl methacrylate
mono or di ethyl itaconate
propyl acrylate
propyl methacrylate
mono or di propyl itaconate
n-butyl acrylate
n-butyl methacrylate
mono or di n-butyl itaconate
isopropyl acrylate
isopropyl methacrylate
mono or di isopropyl itaconate
hexyl acrylate
hexyl methacrylate
mono or di hexyl itaconate
hepyl acrylate
hepyl methacrylate
mono or di hepyl itaconate
cyclohexyl acrylate
cyclohexyl methacrylate
mono or di cyclohexyl itaconate
2-ethylhexyl acrylate
2-ethylhexyl methacrylate
mono or di 2-ethylhexyl itaconate
ethoxyethyl acrylate
ethoxyethyl methacrylate
mono or di ethoxyethyl itaconate
butoxyethyl acrylate
butoxyethyl methacrylate
mono or di butoxyethyl itaconate
2-hydroxy ethyl acrylate
2-hydroxy ethyl methacrylate
mono or di 2-hydroxy ethyl itaconate
2 or 3-hydroxypropyl acrylate
2 or 3-hydroxypropyl methacrylate
mono or di 2 or 3-hydroxypropyl itaconate
3-methoxy-2-hydroxypropyl acrylate
3-methoxy-2-hydroxypropyl methacrylate
mono or di 3-methoxy-2-hydroxypropyl itaconate
tetrahydrofurfuryl acrylate
tetrahydrofurfuryl methacrylate
mono or di tetrahydrofurfuryl itaconate
aryl acrylate
aryl methacrylate
mono or di aryl itaconate
allyl acrylate
allyl methacrylate
mono or di allyl itaconate
glycidoxy acrylate
glycidoxy methacrylate
mono or di glycidoxy itaconate Other comonomers may include hydrophilic wetting agents, N-vinylcarbazole, N-vinylpyrrolidone, hydroxy naphthyl methacrylate, styryls, such as styrene, methylstyrene, methoxy styrene and acetoxy styrene and allylic monomers, such as diallyl diglycol carbonate, diallyl phthalate, diallyl carbonate and triallyl cyanurate.

The wettability of the compositions disclosed in this invention may be enhanced by the inclusion of hydrophilic agents such as neutral monomers, hydrophilic cationic monomers and hydrophilic anionic monomers and mixtures of these referred to as among the hydrophilic wetting agents herein. The classes of these compounds are hydrophilic acrylates and methacrylates, acrylamides, methacrylamides and vinyllactams.

Representative hydrophilic neutral monomers include:
N-vinylpyrrolidone
acrylamide
methacrylamide
2-hydroxyethyl acrylate or methacrylate
2 or 3-hydroxy propyl acrylate or methacrylate
glyceryl acrylate or methacrylate
glycidyl acrylate or methacrylate
3-methoxy-2-hydroxy propyl acrylate or methacrylate
mono esters of acrylic and methacrylic acid with polyethers of the general formula:

$$HO(C_nH_{2n}O)_xH$$

wherein "n" is a number from 1 to about 4 and "x" is a number from 2 to about 10.

The cationic monomers either can be initially in their charged form or are subsequently converted to their charged form after formation of the contact lens. The classes of these compounds are derived from basic or cationic acrylates, methacrylates, acrylamides, methacrylamides, vinylpyridines, vinylimidazoles, and diallyl-dialkylammonium polymerizable groups. Such monomers are represented by:
N,N-dimethylaminoethyl acrylate and methacrylate
2-methacryloyloxyethyltrimethylammonium chloride and methylsulfate
2-,4-, and 2-methyl-5-vinylpyridine
2-,4-, and 2-methyl-5-vinylpyridinium chloride and methylsulfate
N-(3-methacrylamidopropyl)-N,N-dimethylamine
N-(3-methacrylamidopropyl)-N,N,N-trimethylammonium chloride
N-(3-methacryloyloxy-2-hydroxylpropyl)-N,N,N-trimethylammonium chloride
diallyldimethylammonium chloride and methylsulfate The anionic monomers either are in their neutral form initially or are subsequently converted to their anionic form. These classes of compounds include polymerizable monomers which contain carboxy, sulfonate, and phosphate or phosphate groups. Such monomers are represented by:
acrylic acid
methacrylic acid
sodium acrylate and methacrylate
vinylsulfonic acid
sodium vinylsulfonate
p-styrenesulfonic acid
sodium p-styrenesulfonate
2-methacryloyloxyethylsulfonic acid
3-methacryloyloxy-2-hydroxypropylsulfonic acid
2-acrylamido-2-methylpropanesulfonic acid
allylsulfonic acid
2-phosphatoethyl methacrylate Examples of cross-linking agents can be used in forming polymeric materials of this invention and include polyfunctional derivatives of acrylic acid, methacrylic acid, acrylamide, methacrylamide and multi-vinyl substituted benzenes, including but not limited to the following:
ethylene glycol diacrylate or dimethacrylate
diethylene glycol diacrylate or dimethacrylate
tetraethylene glycol diacrylate or dimethacrylate
polyethylene glycol diacrylate or dimethacrylate
polypropylene glycol diacrylate or methacrylate
trimethylolpropane triacrylate or trimethacrylate
Bisphenol A diacrylate or dimethacrylate
ethoxylated Bisphenol A diacrylate or dimethacrylate
pentaerythritol tri- and tetraacrylate or methacrylate
tetramethylenediacrylate or dimethacrylate
methylene bisacrylamide or methacrylamide
dimethylene bisacrylamide or methacrylamide
N,N'-dihydroxyethylene bisacrylamide or methacrylamide
hexamethylene bisacrylamide or methacrylamide
decamethylene bisacrylamide or methacrylamide
divinyl benzene The copolymers described in this invention are prepared by radical polymerization through the incorporation of a free radical initiator. The initiator is chosen from those commonly utilized to polymerize vinyl type monomers and would include the following representative initiators:
2,2'-azo-bis-isobutyronitrile
4,4'-azo-bis-(4-cyanopentanoic acid)
t-butyl peroctoate
benzoyl peroxide
lauroyl peroxide
methyl ethyl ketone peroxide
diisopropyl peroxycarbonate The free radical initiator is normally used in amounts of from 0.01 to 2% by weight of the entire compound.

The materials of this invention can be polymerized directly in a suitable mold to form contact lenses directly. It is preferable to polymerize into sheet or rod stock from which contact lenses may be machined.

It is preferred to use the conventional approach when forming contact lenses such as used for polymethyl methacrylate (PMMA). In this approach, the formulations are polymerized directly into a sheet or rod from which blanks in the form of buttons, discs or other preformed shapes are cut. These blanks are then machined to obtain the lens surfaces. The resulting polymeric stock of blanks possesses the optical qualities necessary to produce aberration-free oxygen-permeable, hard contact lenses in accordance with this invention. Oxygen permeability values of the contact lenses were generated by a procedure as described in ASTM D1434 except that plano contact lenses are used instead of large flat discs of material. The permeability apparatus was constructed in such a manner as to accept actual contact lenses and calibrated with other polymeric lenses of known permeability. As a comparison to the oxygen permability data reported in the Examples, polymethyl methacrylate, polycarbonate, and polystyrene have oxygen permeabilities of 1, 22, and 35 $cm^3mm/cm^2sec\ cmHg \times 10^{-10}$, respectively.

The following examples are given to illustrate the invention and not meant to be limiting

EXAMPLE 1

Synthesis of γ-methacryloxypropyl-tris(3-acetoxypropyldimethylsiloxy)silane

A catalyst solution is prepared by adding, with stirring, 52 ml of concentrated sulfuric acid to a cooled mixture of 59 ml absolute ethanol and 66 ml of distilled water.

A 1000 ml round bottom flask, equipped with a magnetic stirring bar, is placed in a suitable size container which will function as a water bath. To the flask is added 100 ml (0.42 moles) of γ-methacryloxypropyltrimethoxy silane and 300 ml (1.26 moles) of 3-acetoxypropyldimethylacetoxy silane. The bath vessel is filled with water at a temperature of between 20° and 30° C. While stirring, 20 ml of catalyst solution (prepared earlier) is added dropwise from a droping funnel into the flask. After the catalyst addition is complete, the reaction mixture is stirred at room temperature for 72 hours. Approximately two volumes of distilled water are then added to the reaction mixture and the batch washed for several hours. The organic layer is then isolated and stripped of low boiling contaminants by vacuum distillation at a temperature of between 50° and 60° C. The monomer is then decolored with activated carbon yielding approximately 220 ml of γ-methacryloxypropyl-tris(3-acetoxypropylmethylsiloxy)silane.

EXAMPLE 2

Synthesis of γ-methacryloxypropyl-bis(3-acetoxypropyldimethylsiloxy)-(trimethylsiloxy)silane A catalyst solution is prepared by adding, with stirring, 52 ml of concentrated sulfuric acid to a cooled mixture of 59 ml absolute ethanol and 66 ml of distilled water.

A 1000 ml round bottom flask, equipped with a magnetic stirring bar, is placed in a suitable size container which will function as a water bath. To the flask is added 100 ml (0.42 moles) of γ-methacryloxypropyltrimethoxy silane, 65 ml (0.42 moles) trimethylacetoxysilane and 200 ml (0.84 moles) 3-acetoxypropyldimethylacetoxysilane. The bath vessel is filled with water at a temperature of between 20° and 30° C. While stirring, 20 ml of catalyst solution (prepared earlier) is added dropwise from a dropping funnel into the flask. After the catalyst addition is complete, the reaction mixture is stirred at room temperature for 72 hours. The upper oily layer is then isolated and stripped of low boiling contaminants by vacuum distillation at a temperature of between 50° and 60° C. The monomer is then decolored with activated carbon yielding approximately 200 ml of γ-methacryloxy propyl-bis(3-acetoxypropyldimethylsiloxy)(trimethylsiloxy)silane.

EXAMPLE 3

Synthesis of γ-Methacryloxypropyl(3-acetoxypropyl dimethylsiloxy)bis(trimethylsiloxy)silane A catalyst solution is prepared by adding, with stirring, 52 ml of concentrated sulfuric acid to a cooled mixture of 59 ml absolute ethanol and 66 ml of distilled water.

A 1000 ml round bottom flask, equipped with a magnetic stirring bar, is placed in a suitable size container which will function as a water bath. To the flask is added 100 ml (0.42 moles) of γ-methacryloxypropyltrimethoxy silane, 130 ml (0.84 moles) trimethylacetoxysilane and 100 ml (0.42 moles) 3-acetoxypropyldimethylacetoxysilane. The bath vessel is filled with water at a temperature of between 20° and 30° C. While stirring, 20 ml of catalyst solution (prepared earlier) is added dropwise from a dropping funnel into the flask. After the catalyst addition is complete, the reaction mixture is stirred at room temperature for 72 hours. The upper oily layer is separated and washed with two volumes of distilled water. The organic layer is then isolated and stripped of low boiling contaminants by vacuum distillation at a temperature of between 50° and 60° C. The monomer is then decolored with activated carbon yielding approximately 170 ml of γ-methacryloxypropyl(3-acetoxypropyldimethylsiloxy)-bis(trimethylsiloxy)silane.

EXAMPLE 4

Synthesis of γ-methacryloxypropyl-bis(pentamethyldisiloxanyl)(3-acetoxypropyldimethylsiloxy)silane A catalyst solution is prepared by adding, with stirring, 52 ml of concentrated sulfuric acid to a cooled mixture of 59 ml absolute ethanol and 66 ml of distilled water.

A 1000 ml round bottom flask, equipped with a magnetic stirring bar, is placed in a suitable size container which will function as a water bath. To the flask is added 100 ml (0.42 moles) of γ-methacryloxypropyltrimethoxy silane, 210 ml (0.84 moles) pentamethylacetoxydisiloxane and 100 ml (0.42 moles) 3-acetoxypropyldimethylacetoxysilane. The bath vessel is filled with water at a temperature of between 20° and 30° C. While stirring, 20 ml of catalyst solution (prepared earlier) is added dropwise from a dropping funnel into the flask. After the catalyst addition is complete, the reaction mixture is stirred at room temperature for 72 hours. The upper oily layer is separated and washed with two volumes of distilled water. The organic layer is then isolated and stripped of low boiling contaminants by vacuum distillation at a temperature of between 50° and 60° C. The monomer is then decolored with activated carbon yielding approximately 230 ml of γ-methacryloxypropyl-bis(pentamethyldisiloxanyl)(3-acetoxypropyl dimethylsiloxy)silane.

EXAMPLE 5

Synthesis of 1,3-Bis(γ-methacryloxypropyl)-1,1,3,3 tetra (3-acetoxypropyldimethylsiloxy)disiloxane A catalyst solution is prepared by adding, with stirring, 52 ml of concentrated sulfuric acid to a cooled mixture of 59 ml absolute ethanol and 66 ml of distilled water.

A 1000 ml round bottom flask, equipped with a magnetic stirring bar, is placed in a suitable size container which will function as a water bath. To the flask is added 100 ml (0.42 moles) of γ-methacryloxypropyltrimethoxysilane and 200 ml (0.84 moles) of 3-acetoxypropyldimethyl acetoxy silane. The bath vessel is filled with water at a temperature of between 20° and 30° C. While stirring, 20 ml of catalyst solution (prepared earlier) is added dropwise from a dropping funnel into the flask. After the catalyst addition is complete, the reaction mixture is stirred at room temperature for 72 hours. Approximately two volumes of distilled water are then added to the reaction mixture and the batch washed for several hours. The organic layer is then isolated and stripped of low boiling contaminants by vacuum distillation at a temperature of between 50° and 60° C. The monomer is then decolored with activated carbon yielding approximately 100 ml of 1,3-Bis(γ-methacryloxypropyl)-1,1,3,3 tetra(3-acetoxypropyldimethylsiloxy)-disiloxane.

EXAMPLE 6

Synthesis of 1-(γ-methacryloxypropyl)-3-(3-acetoxypropyl)-tetra(-trimethylsiloxy)disiloxane A catalyst solution is prepared by adding, with stirring, 52 ml of concentrated sulfuric acid to a cooled mixture of 59 ml absolute ethanol and 66 ml of distilled water.

A 1000 ml round bottom flask, equipped with a magnetic stirring bar, is placed in a suitable size container which will function as a water bath. To the flask is added 100 ml (0.42 moles) of γ-methacryloxypropyl-trimethoxy silane, 248 ml (1.68 moles) trimethylacetoxysilane and 96 ml (0.42 moles) 3-acetoxypropyltrimethoxysilane. The bath vessel is filled with water at a temperature of between 20° and 30° C. While stirring, 40 ml of catalyst solution (prepared earlier) is added dropwise from a dropping funnel into the flask. After the catalyst addition is complete, the reaction mixture is stirred at room temperature for 72 hours. The upper oily layer is separated and washed with two volumes of distilled water. The organic layer is then isolated and stripped of low boiling contaminants by vacuum distillation at a temperature of between 50° and 60° C. The monomer is then decolored with activated carbon yielding approximately 150 ml of 1-(γ-methacryloxypropyl)-3-(3-acetoxypropyl)-tetra(trimethylsiloxy)disiloxane.

EXAMPLE 7

A mixture of 20 parts of the substituted polysiloxane of Example 1 (A3TRIS), 80 parts of methylmethacrylate (MMA) and 0.4 parts of α,α'-azobisisobutyronitrile (AIBN) is placed in test tubes which are purged with nitrogen then sealed with a serum cap. The test tubes are placed in a water bath at 40° C. and allowed to polymerize for 3 days. The tubes are then placed in a 65° C. oven for an additional time period of 3 days, after which the polymerized rods are removed from the tubes. The hard, transparent rods are then subjected to conditioning for approximately 24 hours at 100° C. under vacuum to complete the polymerization process and relieve any mechanical stresses present. The conditioned rods are then machined to contact lens blanks (a disk ½ inch in diameter by 3/16 inch thick). The Rockwell hardness of this material is 119 on the R scale (ASTM D-785).

A contact angle measurement obtained by placing a drop of water on the polished flat surface indicates a contact angle of 59 degrees.

The oxygen permeability of a 0.20 mm thick contact lens is 25 $cm^3$ $mm/cm^2 sec$ $cm$ $Hg \times 10^{-10}$ when measured by the method described in the specification.

EXAMPLE 8

A mixture of 40 parts of the substituted polysiloxane monomer of Example 1 (A3TRIS), 60 parts of methylmethacrylate (MMA) 2 parts of tetraethylene glycol dimethacrylate (TGD) and 0.4 parts of α,α'-azobisisobutyronitrile (AIBN) is placed in test tubes which are purged with nitrogen then sealed with serum caps. The test tubes are placed in a water bath at 40° C. and allowed to polymerize for 3 days. The tubes are then placed in a 65° C. oven for an additional time period of 3 days, after which the polymerized rods are removed from the tubes. The hard transparent rods are then subjected to conditioning for approximately 24 hours at 100° C. under vacuum to complete the polymerization process and relieve any mechanical stresses present. The conditioned rods are then machined to contact lens blanks (a disk ½ inch in diameter by 3/16 inch thick). The Rockwell Hardness of this material is 119 on the R scale (ASTM D-785).

A contact angle measurement obtained by placing a drop of water on the polished flat surface indicates a contact angle of 58 degrees.

The oxygen permeability of a 0.20 mm thick contact lens is 56 $cm^3$ $mm/cm^2 sec$ $cm$ $Hg \times 10^{-10}$ when measured by the method described in the specification.

EXAMPLE 9

Utilizing the experimental procedure of Example 7 this Example illustrates the preparation and properties of copolymer containing varying proportions of the substituted polysiloxane monomer of Example 3 (AITRIS) and methylmethacrylate (MMA).

| Composition (wt. %) | | | Properties |
|---|---|---|---|
| MMA | AITRIS | AIBN | |
| 39.9 | 59.9 | 0.2 | T, H, R |
| 29.9 | 69.9 | 0.2 | T, SR |
| 19.9 | 79.9 | 0.2 | T, S |
| 0 | 99.8 | 0.2 | T, E |

T = Transparent
H = Hard
R = Rigid
S = Soft
E = Elastomeric

EXAMPLE 10

Utilizing the experimental procedures of example 7, this Example illustrates the preparation and properties of hard contact lenses in which the level of substituted polysiloxane monomer (ALTRIS) is changed.

| Composition (wt. %) | | | | | HARDNESS | OXYGEN |
|---|---|---|---|---|---|---|
| MMA | AITRIS | MA* | TGD** | AIBN | ROCKWELL R | PERMEABILITY*** |
| 56.5 | 37.7 | 4.7 | 0.9 | 0.2 | 112 | 46 |
| 51.8 | 42.4 | 4.7 | 0.9 | 0.2 | 107 | 67 |
| 47.1 | 47.1 | 4.7 | 0.9 | 0.2 | 100 | 108 |

*Methacrylic acid
**Tetraethyleneglycol dimethacrylate
***Value in $cm^3$ $mm/cm^2$ sec cm Hg $\times 10^{10}$

EXAMPLE 11

Utilizing the experimental procedures of Example 7, this Example illustrates the preparation and properties of materials suitable for semi-rigid contact lenses.

| Composition (wt. %) | | | | | |
|---|---|---|---|---|---|
| MMA | A2TRIS | MA | TEDGM | AIBN | PROPERTIES |
| 49.4 | 49.4 | 0.0 | 1.0 | 0.2 | T, SR |

-continued

| Composition (wt. %) | | | | | PROPERTIES |
|---|---|---|---|---|---|
| MMA | A2TRIS | MA | TEDGM | AIBN | |
| 47.1 | 47.1 | 4.7 | 0.9 | 0.2 | T, SR |

T = Transparent
SR = Semi-rigid

EXAMPLE 12

A mixture of 24.7 parts of the polysiloxane monomer of Example 3 (AITRIS), 74.1 parts of methoxyethylacrylate (MEA), 1.0 parts of tetraethylene glycol diemthacrylate (TGD) and 0.2 parts of $\alpha,\alpha$-azobisisobutyronitrile (AIBN) is polymerized in a test tube, under nitrogen in a stepwise fashion. The polymerization schedule was 3 days at 40° C., 3 days at 65° C. then 1 day at 100° C. under vacuum. The resultant plug is transparent, flexible and suitable as a soft contact lens material.

EXAMPLE 13

A mixture of 49.4 parts of the polysiloxane monomer of Example 3 (AITRIS), 49.4 parts of methoxyethylacrylate (MEA), 1.0 parts of tetraethylene glycol dimethacrylate (TGD) and 0.2 parts of $\alpha,\alpha$-azobisisobutyronitrile (AIBN) is polymerized in a test tube, under nitrogen in a stepwise fashion. The polymerization schedule was 3 days at 40° C., 3 days at 65° C. then 1 day at 100° C. under vacuum. The resultant plug is transparent, flexible and suitable as a soft contact lens material.

EXAMPLE 14

A mixture of 24.7 parts of the polysiloxane monomer of Example 3 (AITRIS), 74.1 parts of butoxyethylmethacrylate (BEM), 1.0 parts of tetraethylene glycol dimethacrylate (TGD) and 0.2 parts of $\alpha,\alpha$-azobisisobutyronitrile (AIBN) is polymerized in a test tube, under nitrogen, in a stepwise fashion. The polymerization schedule was 3 days at 40° C., 3 days at 65° C. then 1 day at 100° C. under vacuum. The resultant plug is transparent, flexible and suitable as a soft contact lens material.

EXAMPLE 15

A mixture of 49.4 parts of the polysiloxane monomer of Example 3 (AITRIS), 49.4 parts of butoxyethylmethacrylate (BEM), 1.0 parts of tetraethylene glycol dimethacrylate (TGD) and 0.2 parts of $\alpha,\alpha$-azobisisobutyronitrile (AIBN) is polymerized in a test tube, under nitrogen, in a stepwise fashion. The polymerization schedule was 3 days at 40° C., 3 days at 65° C. then 1 day at 100° C. under vacuum. The resultant plug is transparent, flexible and suitable as a soft contact lens material.

EXAMPLE 16

A mixture of 49.4 parts of polysiloxane monomer of Example 1 (A3TRIS), 49.4 parts of butoxyethylmethacrylate (BEM), 1.0 parts of tetraethylene glycol dimethacrylate (TGD) and 0.2 parts of $\alpha,\alpha$-azobis-isobutyronitrile (AIBN) is polymerized in a test tube, under nitrogen, in a stepwise fashion. The polymerization schedule was 3 days at 40° C., 3 days at 65° C. then 1 day at 100° C. under vacuum. The resultant plug is transparent, flexible and suitable as a soft contact lens material.

EXAMPLE 17

A mixture of 74.1 parts of the polysiloxane monomer of Example 1 (A3TRIS), 24.7 parts of butoxyethylmethacrylate (BEM), 1.0 parts of tetraethylene glycol dimethacrylate (TGD) and 0.2 parts of $\alpha,\alpha$-azobis-isobutyronitrile (AIBN) is polymerized in a test tube, under nitrogen, in a stepwise fashion. The polymerization schedule was 3 days at 40° C., 3 days at 65° C. then 1 day at 100° C. under vacuum. The resultant plug is transparent, flexible and suitable as a soft contact lens material.

EXAMPLE 18

Utilizing the experimental procedures of Example 7 this Example illustrates the preparation and properties of copolymers containing various proportions of the substituted monomer of Example 4 (P2ATRIS), methylmethacrylate (MMA), methacrylic acid (MA) and tetraethyleneglycol-dimethacrylate (TGD).

| Composition (Wt. %) | | | | | HARDNESS |
|---|---|---|---|---|---|
| MMA | P2ATRIS | MA | TGD | AIBN | ROCKWELL R |
| 63.9 | 35.0 | — | 0.9 | 0.2 | 116 |
| 53.9 | 45.0 | — | 0.9 | 0.2 | 108 |
| 48.9 | 50.0 | — | 0.9 | 0.2 | 96 |
| 53.0 | 43.5 | 2.4 | 0.9 | 0.2 | 110 |
| 50.7 | 43.5 | 4.7 | 0.9 | 0.2 | 113 |

EXAMPLE 19

Utilizing the experimental procedures of Example 7 this Example illustrates the preparation and properties of copolymer containing varying proportions of the substituted monomer of Example 5 (A4D) and Methylmethacrylate (MMA).

| Composition (wt. %) | | | Properties |
|---|---|---|---|
| MMA | A4D | AIBN | |
| 59.8 | 40.0 | 0.2 | T, H |
| 49.8 | 50.0 | 0.2 | T, H |
| 39.8 | 60.0 | 0.2 | T, H |
| 29.8 | 70.0 | 0.2 | T, H |

T = Transparent
H = Hard

EXAMPLE 20

A mixture of 50 parts of the polysiloxane monomer of Example 6, 45 parts of methylmethacrylate, 5 parts of methacrylic acid and 0.2 parts of $\alpha,\alpha'$-azobisisobutyronitrile was polymerized according to the procedures set forth in Example 7. The resultant polymer was hard and transparent and suitable as a hard contact lens material. The Rockwell R Hardness of the material was 113 and the oxygen permeability was found to be 150. Contact lenses machined from this material were found to be dimensionally stable and wettable by human tears.

The following Table illustrates the general combinations of materials as preferred for use in the present invention to form polymerized organosiloxane materials in a form suitable for machining or casting as contact lenses:

| Oxygen Permeable Siloxane Material | Formulation 1 | Formulation 2 | Formulation 3 |
|---|---|---|---|
| Oxygen permeable siloxane material of this invention | 100% | 25–98% | 25–98% |
| Hardening Agent | 0 | 75–2% | 75–1% |
| Hydrophilic agent | 0 | 0 | 1%–10% |

The polysiloxanes of this invention can be used in place of the siloxane materials of prior art lens polymeric combinations. For example, the siloxanes of this invention can be used instead of the siloxanyl alkyl esters in the contact lens formulations of U.S. Pat. No. 4,152,508 issued May 1, 1979.

The above Examples are merely illustrative of the present invention. Many combinations are possible. Both hard, semi-hard, and soft contact lenses ca be advantageously produced using the compositions of this invention.

Usual additives such as tints, colorants, antioxidants, stabilizers, absorbers and the like can be incorporated in the formulations of this invention if desired. All lenses can have conventional hardening agents, softening agents, wetting agents, hydrophilic hardening agents and the like incorporated therein so long as desired contact lens properties are retained. Both hard and soft lenses can be made depending on the additives, if any, used with the polysiloxanes of this invention.

I claim:

1. A contact lens material formed of a siloxane containing one or more unsaturated polymerizable groups for use in contact lens having high oxygen permeability, dimensional stability, inherent wettability, high light transmission, durability, biocompatibility, non-hydrating, chemical stability, and high resistance to proteinaceous accumulation as well as being scratch resistant having the following formula:

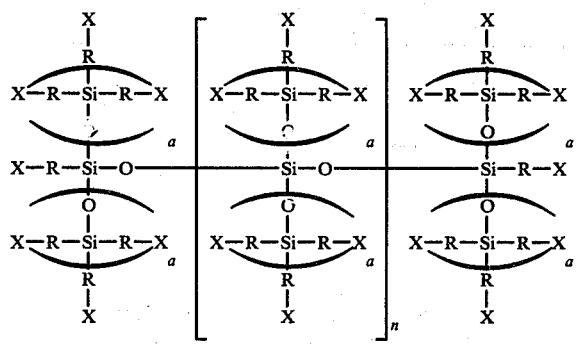

wherein:
X is selected from the group consisting essentially of unsaturated polymerizable methacrylate, acrylate, hydrogen or "Z" groups and mixtures thereof,
R is selected from the group consisting essentially of alkylene, cycloalkylene groups having from 1 to about 10 carbon atoms, arylene groups and mixtures thereof,
a is an integer from 0 to about 10 where each "a" may be the same or different,
n is an integer from 0 to about 10,
Z groups are selected from the group consisting essentially of acetoxy, carbomethoxy, glycidoxy, glyceryl, and carboxy with at least one "X" being a "Z" group.

2. A contact lens material in accordance with claim 1 wherein said siloxane is 1,3-bis(γ-methacryloxypropyl-1,1,3,3-tetra(3-acetoxypropyldimethylsiloxy)disiloxane.

3. A contact lens material in accordance with claim 1 wherein said siloxane is γ-methacryloxypropyl-tris(4-acetoxyphenyldimethylsiloxy)silane.

4. A contact lens material in accordance with claim 1 wherein said siloxane is γ-methacryloxypropyl-tris(2-carboxyethyldimethylsiloxy)silane.

5. A contact lens material in accordance with claim 1 wherein said siloxane is γ-methacryloxypropyl-tris(2-acetoxyethyldimethylsiloxy)silane.

6. A contact lens material in accordance with claim 1 wherein said siloxane is 1-γ-methacryloxymethyl-3-(3-acetoxypropyl)-1,1,3,3-tetramethyldisiloxane.

7. A contact lens material in accordance with claim 1 wherein said siloxane is γ-methacryloxypropyl-bis(-trimethylsiloxy)-(3-acetoxypropyldimethylsiloxy)silane.

8. A contact lens material in accordance with claim 1 wherein said siloxane is γ-methacryloxypropyl-bis(-trimethylsiloxy)-(3-carbomethoxypropyldimethylsiloxy)silane.

9. A contact lens material in accordance with claim 1 wherein said siloxane is γ-methacryloxypropyl-bis(-trimethylsiloxy)-(3-hydroxypropyldimethylsiloxy)silane.

10. A contact lens material in accordance with claim 1 wherein said siloxane is γ-methacryloxypropyl-bis(-trimethylsiloxy)-(3-carboxypropyldimethylsiloxy)silane.

11. A contact lens material in accordance with claim 1 wherein said siloxane is γ-methacryloxypropyl-bis(3-acetoxypropyldimethylsiloxy)-(trimethylsiloxy)silane.

12. A contact lens material in accordance with claim 1 wherein said siloxane is γ-methacryloxypropyl-bis(3-carbomethoxypropyldimethylsiloxy)-(trimethylsiloxy)silane.

13. A contact lens material in accordance with claim 1 wherein said siloxane is γ-methacryloxypropyl-bis(3-hydroxypropyldimethylsiloxy)-(trimethylsiloxy)silane.

14. A contact lens material in accordance with claim 1 wherein said siloxane is γ-methacryloxypropyl-bis(3-carboxypropyldimethylsiloxy)-(trimethylsiloxy)silane.

15. A contact lens material in accordance with claim 1 wherein said siloxane is γ-methacryloxypropyl-tris(3-acetoxypropyldimethylsiloxy)silane.

16. A contact lens material in accordance with claim 1 wherein said siloxane is γ-methacryloxypropyl-tris(3-carbomethoxypropyldimethylsiloxy)silane.

17. A contact lens material in accordance with claim 1 wherein said siloxane is γ-methacryloxypropyl-tris(3-hydroxypropyldimethylsiloxy)silane.

18. A contact lens material in accordance with claim 1 wherein said siloxane is γ-methacryloxypropyl-bis(-pentamethyldisiloxanyl)-(3-acetoxypropyldimethylsiloxy)silane.

19. A contact lens material in accordance with claim 1 wherein said siloxane is γ-methacryloxypropyl-bis(-pentamethyldisiloxanyl)-(3-carbomethoxypropyldimethylsiloxy)silane.

20. A contact lens material in accordance with claim 1 wherein said siloxane is γ-methacryloxypropyl-bis(-pentamethyldisiloxanyl)-(3-hydroxypropyldimethylsiloxy)silane.

21. A contact lens material in accordance with claim 1 wherein said siloxane is γ-methacryloxypropyl-bis-(pentamethyldisiloxanyl)-(3-carboxypropyldimethylsiloxy)silane.

22. A contact lens material in accordance with claim 1 wherein said siloxane is 1-(γ-methacryloxypropyl)-3-(3-acetoxypropyl)-tetra(trimethylsiloxy)disiloxane.

23. A contact lens material in accordance with claim 1 wherein said siloxane is 1-(γ-methacryloxypropyl)-3-(3-carbomethoxypropyl)-tetra(trimethylsiloxy)disiloxane.

24. A contact lens material in accordance with claim 1 wherein said siloxane is 1-(γ-methacryloxypropyl)-3-(3-hydroxypropyl)-tetra(trimethylsiloxy)disiloxane.

25. A contact lens material in accordance with claim 1 wherein said siloxane is 1-(γ-methacryloxypropyl)-3-(3-carboxypropyl)-tetra(trimethylsiloxy)disiloxane.

26. A contact lens formed of a siloxane containing one or more unsaturated polymerizable groups having the following formula:

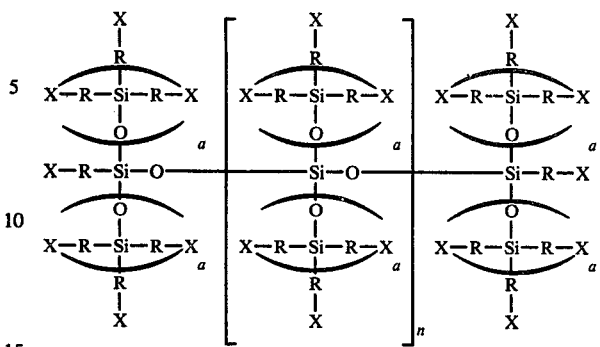

wherein:
X is selected from the group consisting essentially of unsaturated polymerizable methacrylate, acrylate, hydrogen or "Z" groups and mixtures thereof,
R is selected from the group consisting essentially of alkylene, cycloalkylene groups having from 1 to about 10 carbon atoms, arylene groups and mixtures thereof,
a is an integer from 0 to about 10 where each "a" may be the same or different,
n is an integer from 0 to about 10,
Z groups are selected from the group consisting essentially of acetoxy, carbomethoxy, glycidoxy, glyceryl, and carboxy with at least one "X" being a "Z" group.

27. A contact lens in accordance with claim 26 wherein said siloxane is copolymerized with a hardening agent.

28. A contact lens in accordance with claim 26 wherein said siloxane is copolymerized with a wetting agent.

29. A contact lens in accordance with claim 28 and further including a hardening agent.

30. A contact lens in accordance with claim 29 wherein said hardening agent is selected from the group consisting of acrylic, methacrylic acid itaconic acid derivatives including esters of a $C_1$–$C_{20}$ monohydric or polyhydric alkanol, phenol and an acid selected from the class consisting essentially of acrylic and methacrylic acid, itaconate mono and diester.

31. A contact lens in accordance with claim 30 wherein said wetting agent is selected from the group consisting of neutral monomers, hydrophilic cationic monomers and hydrophilic anionic monomers.

* * * * *